(12) United States Patent
Komiyama

(10) Patent No.: US 11,400,017 B2
(45) Date of Patent: Aug. 2, 2022

(54) LIQUID MEDICINE SUPPLY DEVICE

(71) Applicant: KOBAYASHI PHARMACEUTICAL CO., LTD., Osaka (JP)

(72) Inventor: Satoru Komiyama, Osaka (JP)

(73) Assignee: KOBAYASHI PHARMACEUTICAL CO., LTD., Osaka (JP)

( * ) Notice: Subject to any disclaimer, the term of this patent is extended or adjusted under 35 U.S.C. 154(b) by 334 days.

(21) Appl. No.: 16/495,067

(22) PCT Filed: Mar. 22, 2018

(86) PCT No.: PCT/JP2018/011400
§ 371 (c)(1),
(2) Date: Sep. 17, 2019

(87) PCT Pub. No.: WO2018/174155
PCT Pub. Date: Sep. 27, 2018

(65) Prior Publication Data
US 2020/0093691 A1 Mar. 26, 2020

(30) Foreign Application Priority Data
Mar. 23, 2017 (JP) .............. JP2017-057551

(51) Int. Cl.
*A61J 1/14* (2006.01)
*B65D 50/04* (2006.01)
*A61M 35/00* (2006.01)

(52) U.S. Cl.
CPC .......... *A61J 1/1418* (2015.05); *A61M 35/003* (2013.01); *B65D 50/041* (2013.01); *B65D 2215/02* (2013.01)

(58) Field of Classification Search
CPC . A61J 1/1418; B65D 50/041; B65D 2215/02; A61M 35/003
(Continued)

(56) References Cited

U.S. PATENT DOCUMENTS 3,795,338 A * 3/1974 Swartzbaugh ....... B65D 50/041
215/220
4,410,098 A 10/1983 Dubs et al.
(Continued)

FOREIGN PATENT DOCUMENTS

CN 103025302 A 4/2013
JP H58-11660 A 1/1983
(Continued)

OTHER PUBLICATIONS

English translation of JP 2014-221655 provided by Espacenet. http://translationportal.epo.org/emtp/translate?ACTION=description-retrieval&COUNTRY=JP&ENGINE=google&FORMAT=docdb&KIND=A&LOCALE=en_EP&NUMBER=2014221665&OPS=ops.epo.org%2F3.2&SRCLANG=ja&TRGLANG=en&apikey=TSMqTfrVAvNtryGI8Qlfbozj8DnAGIqJ&PDF=.*
(Continued)

*Primary Examiner* — James N Smalley
(74) *Attorney, Agent, or Firm* — Kratz, Quintos & Hanson, LLP

(57) ABSTRACT

[Object] It is an object of the present invention to provide a liquid medicine supply device configured to reliably prevent infants and children from accidentally opening the liquid medicine supply device.
[Solutions] A liquid medicine supply device (1) including a container (10) with a containing portion (11) and a mouth (16); an interior cap (30); and an exterior cap (60), in which the interior and exterior caps (30, 60) include a ratchet mechanism (50, 80). The ratchet mechanism allows the exterior and interior caps (60, 30) to be integrally rotated when the exterior cap is rotated relative to the mouth under a condition of the exterior cap (60) pressed against the interior cap whereas the ratchet mechanism allows the exterior cap (60) to be rotated relative to the interior cap (30) when the exterior cap is rotated relative to the mouth under
(Continued)

a condition of the exterior cap (60) which is not pressed against the interior cap. An axial direction of the mouth (16) is inclined from an axial direction of the containing portion (11) at a predetermined angle (θ).

13 Claims, 12 Drawing Sheets

(58) Field of Classification Search
USPC .......................................................... 215/220
See application file for complete search history.

(56) References Cited

U.S. PATENT DOCUMENTS

| | | | | |
|---|---|---|---|---|
| 4,523,688 | A * | 6/1985 | Puresevic | B65D 50/041 |
| | | | | 215/220 |
| 5,370,251 | A * | 12/1994 | Buono | B65D 50/041 |
| | | | | 215/220 |
| 8,316,622 | B2 * | 11/2012 | Jajoo | B65D 50/041 |
| 2009/0250425 | A1 | 10/2009 | Yoshihiro | |
| 2011/0284415 | A1 | 11/2011 | Balakier | |
| 2014/0014611 | A1 | 1/2014 | Buehler et al. | |

FOREIGN PATENT DOCUMENTS

| | | |
|---|---|---|
| JP | S60-097143 U | 7/1985 |
| JP | H02-001656 U | 1/1990 |
| JP | 2000-043909 A | 2/2000 |
| JP | 2001-097435 A | 4/2001 |
| JP | 2001-278318 A | 10/2001 |
| JP | 2004-236702 A | 8/2004 |
| JP | 2007-076676 A | 3/2007 |
| JP | 2014221655 A * | 11/2014 |
| JP | 2015-527268 A | 9/2015 |

OTHER PUBLICATIONS

Office Action of Japanese Patent Application No. 2017-057551: Notification of Reasons for Refusal dated May 12, 2021 (4 sheets, 4 sheets translation, 8 sheets total).
International Search Report for International Patent Application No. PCT/JP2018/011400 dated Jun. 12, 2018 (3 sheets, 2 sheets translation, 5 sheets total).

* cited by examiner

LIQUID MEDICINE SUPPLY DEVICE

TECHNICAL FIELD

The present invention relates to a liquid medicine supply device configured to supply liquid medicine to a supplied part such as the skin.

BACKGROUND ART

A child resistant mechanism (child-proof mechanism) has been known for liquid medicine supply devices used for supplying liquid medicine to a supplied part and liquid medicine containing devices which contain liquid medicine, the child resistant mechanism being configured to prevent infants and children from accidentally opening the liquid medicine supply devices and the liquid medicine containing devices. For example, Patent Literature 1 discloses a liquid medicine containing device including a tubular container which contains liquid medicine, an interior cap connected to a mouth of the container, and an exterior cap covering the interior cap. The interior and exterior caps include a ratchet mechanism as the child resistant mechanism. In detail, ratchet teeth are on an outer curved surface of the interior cap at regular intervals in the circumferential direction whereas ratchet protrusions are on an inner curved surface of the exterior cap at regular intervals in the circumferential direction. The ratchet protrusions engage with the ratchet teeth. The ratchet protrusions are engaged with the ratchet teeth when the exterior cap is pressed against the interior cap.

The exterior and interior caps of the liquid medicine containing device are rotated relative to the mouth of the container when the exterior cap is pressed against the interior cap (the ratchet protrusions engage with the ratchet teeth) and then rotated relative to the mouth of the container. On the other hand, when the exterior cap is rotated relative to the mouth of the container under a condition of the exterior cap which is not pressed against the interior cap, the exterior cap is rotated relative to the interior cap (without engagement of the ratchet protrusions with the ratchet teeth). In short, the exterior and interior caps of the liquid medicine containing device are removed from the container (opened) only when the exterior cap is rotated relative to the mouth under a condition of the exterior cap pressed against the interior cap of the container.

CITATION LIST

Patent Literature

Patent Literature 1: JP 2007-76676 A

SUMMARY OF INVENTION

Problems to be Solved by the Invention

Such a liquid medicine containing device as described in Patent Literature 1 may be opened by infants and children. Likewise, this may happen to a liquid medicine supply device for supplying liquid medicine.

It is an object of the present invention to provide a liquid medicine supply device configured to reliably prevent infants and children from accidentally opening the liquid medicine supply device.

Solutions to the Problems

As a result of intensive investigations for solving the aforementioned problems by the present inventor, it has been figured out that if an axial direction of a container corresponds to an axial direction of a mouth (cap), a pressing force on the exterior cap is likely to act on the container. For example, when an external force in an opening direction of the exterior cap of the liquid medicine supply device on a table acts on the exterior cap under a condition of the exterior cap pressed toward the table with a hand (under engagement of the ratchet mechanism), the container opens. It has been found by the present inventor that this operation is achieved by one hand, which results in accidental opening by infants and children. The present inventor has found that infants and children are prevented from accidentally opening the container (prevention from unintentional engagement of the ratchet mechanism) when a pressing direction on the exterior cap is inclined from an axial direction of the container.

The present invention is made on the basis of such an idea. In detail, a liquid medicine supply device according to one aspect of the present invention includes a container including a tubular containing portion for containing liquid medicine, and a cylindrical mouth connected to the containing portion, the cylindrical mouth including a male thread; an interior cap including a female thread configured to be engaged with the male thread of the mouth, the interior cap having a shape operable to close an opening of the mouth; and an exterior cap attached to an outside of the interior cap. The interior and exterior caps include a ratchet mechanism. The ratchet mechanism allows the exterior and interior caps to be integrally rotated when the exterior cap is rotated relative to the mouth under a condition of the exterior cap pressed against the interior cap whereas the ratchet mechanism allows the exterior cap to be rotated relative to the interior cap when the exterior cap is rotated relative to the mouth under a condition of the exterior cap which is not pressed against the interior cap. An axial direction of the mouth is inclined from an axial direction of the containing portion by a predetermined angle.

With regard to the present liquid medicine supply device, the central axis of the mouth is inclined from the axial direction of the containing portion at a predetermined angle. Therefore, in order to press the exterior cap against the interior cap or the mouth with one hand, it is required that an external force resisting the pressing force is applied to the containing portion. Accordingly, in order to remove the interior and exterior caps from the mouth, an operation to rotate the exterior cap relative to the mouth in an opening direction is required under a condition of the containing portion held with one hand and the exterior cap pressed against the interior cap or the mouth with the other hand (the ratchet mechanism engages). Therefore, infants and children are prevented from accidentally opening the liquid medicine supply device.

Preferably, the containing portion may include a body which is longer in length in first directions perpendicularly intersecting the axial direction of the containing portion than in second directions perpendicularly intersecting both the axial direction and the first direction. The opening of the mouth may face any one of the first directions.

According to the aforementioned configuration, a pressing force on the exterior cap is likely to act toward the interior cap (mouth) with one hand under a condition of the body held with the other hand. Therefore, it become easy for adults to intentionally remove the exterior and interior caps.

In this case, preferably, the container may include a neck between the containing portion and the mouth. The exterior cap may be larger in outer diameter than the neck.

According to the aforementioned configuration, it is less likely that the fingers holding the exterior cap interfere with the neck. Therefore, the exterior cap is easily opened or closed.

With regard to the liquid medicine supply device, preferably, the interior cap may include:

an interior-cap main body including the female thread, the interior-cap main body having a shape operable to close the opening of the mouth; and an engaging portion on an outer surface of the interior-cap main body. The interior-cap main body may include an inner arrangement surface on which the engaging portion is arranged. The engaging portion may protrude toward the exterior cap from the inner arrangement surface in an axial direction of the interior-cap main body. The exterior cap may include: an exterior-cap main body having a shape operable to cover the interior-cap main body; and an engaged portion on an inner surface of the exterior-cap main body, the engaged portion having a shape operable to be engaged with the engaging portion. The engaged portion and the engaging portion may constitute the ratchet mechanism. The exterior-cap main body may include an outer arrangement surface on which the engaged portion is arranged. The engaged portion may protrude toward the interior cap from the outer arrangement surface in an axial direction of the exterior-cap main body. The engaging portion may include: an open-time-pressed-surface configured to be pressed by the engaged portion when the exterior-cap main body is rotated in a direction to open the exterior-cap main body under a pressed state of the exterior-cap pressed against the interior-cap main body, a close-time-pressed-surface configured to be pressed by the engaged portion when the exterior-cap main body is rotated in a direction to close the exterior-cap main body under the pressed state. The engaged portion may include: an open-time-pressing-surface configured to press the open-time-pressed-surface when the exterior-cap main body is rotated in the direction to open the exterior-cap main body under the pressed state, and a close-time-pressing-surface configured to press the close-time-pressed-surface when the exterior-cap main body is rotated in the direction to close the exterior-cap main body under the pressed state.

According to the aforementioned configuration, a structure is obtained, the structure allowing integral rotation of the exterior and interior caps relative to the mouth only when the exterior-cap main body is rotated under the pressed state.

In this case, preferably, the inner arrangement surface may have a shape perpendicularly intersecting the axial direction of the interior-cap main body. An angle defined between the open-time-pressed-surface and the inner arrangement surface may be in a range of 1.57 to 10 times as large as the predetermined angle. The outer arrangement surface may have a shape perpendicularly intersecting the axial direction of the exterior-cap main body. An angle defined between the open-time-pressing-surface and the outer arrangement surface may be in a range of 1.57 to 10 times as large as the predetermined angle.

According to the aforementioned configuration, it becomes easy to intentionally remove the exterior and interior caps. In detail, since the axial direction of the mouth is inclined from the axial direction of the containing portion at a predetermined angle, it is less likely that a pressing force on the exterior-cap main body acts on the interior-cap main body. However, since the angles defined between the open-time-pressed-surface and the inner arrangement surface and between the open-time-pressing-surface and the outer arrangement surface are in the range of 1.57 to 10 times as large as the predetermined angle, a force transmitted from the open-time-pressing-surface to the open-time-pressed-surface is obtained when the exterior-cap main body is rotated under the pressed state.

In this case, preferably, an angle defined between the close-time-pressed-surface and the inner arrangement surface may be in a range of 0.86 to 7.33 times as large as the predetermined angle. An angle defined between the close-time-pressing-surface and the outer arrangement surface may be in a range of 0.86 to 7.33 times as large as the predetermined angle.

According to the aforementioned configuration, the mouth is reliably closed by the exterior and interior caps. The mouth is easily closed even under a worn condition of the close-time-pressing-surface.

With regard to the aforementioned liquid medicine supply device, preferably, the interior-cap main body may include: an interior-cap circular wall including the female thread; an interior-cap upper wall connected to an upper end of the interior-cap circular wall; and a contact ring protruding toward the mouth from an inner surface of the interior-cap upper wall to come into contact with the mouth or a stopper attached to the mouth so that the contact ring tightly closes the container, the contact ring having an annular shape around a central axis of the interior-cap circular wall. The contact ring may be distant from the engaging portion in a radial direction of the interior-cap circular wall.

According to the aforementioned configuration, the engaging portion does not cause sink marks on the contact ring. Therefore, the container is tightly sealed.

In detail, it is preferable that the inner arrangement surface is a part of an outer surface of the interior-cap circular wall, the inner arrangement surface being formed at a portion outside the contact ring in the radial direction of the interior-cap circular wall.

According to the aforementioned configuration, it becomes easy to open or close the exterior and interior caps due to a larger torque transmitted from the exterior-cap main body to the interior-cap main body in comparison to a configuration in which the engaging portion is on an outer surface of a part of the interior-cap main body, the outer surface being situated at an inner side in the radial direction of the interior-cap circular wall than the contact ring.

With regard to the aforementioned liquid medicine supply device, preferably, the engaging portion may be distant from the female thread in an axial direction of the interior-cap circular wall.

According to the aforementioned, the engaging portion does not cause sink marks on the female thread.

Advantageous Effect of the Invention

As described above, according to an aspect of the present invention, a liquid medicine supply device is provided, the liquid medicine supply device being configured to reliably prevent infants and children from accidentally opening the liquid medicine supply device.

DESCRIPTION OF EMBODIMENT

A liquid medicine supply device 1 according to an embodiment of the present invention is described with reference to FIGS. 1 to 12. The liquid medicine supply device 1 supplies a liquid medicine to a supplied part such as the skin. The liquid medicine supply device 1 includes what is called a child resistant mechanism (child-proof mechanism) configured to prevent infants and children from accidentally opening the liquid medicine supply device 1. The liquid medicine supply device is not limited to a specific posture in usage. Hereinafter, however, the vertical direction is defined on the basis of the vertical direction in FIG. 1, for convenience.

Figure 1:
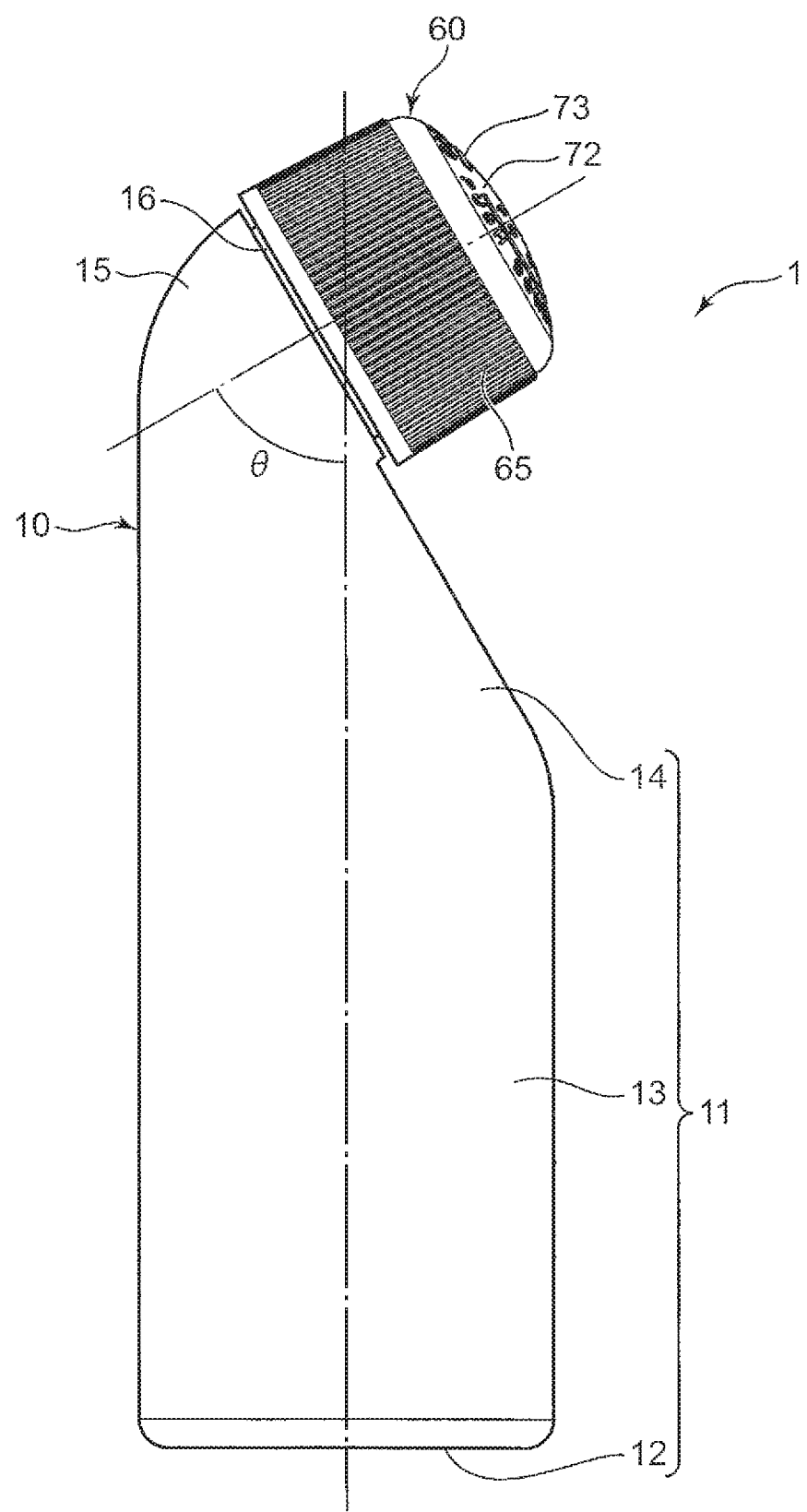
FIG. 1 is a front view of a liquid medicine supply device according to an embodiment of the present invention.
Figure 4:
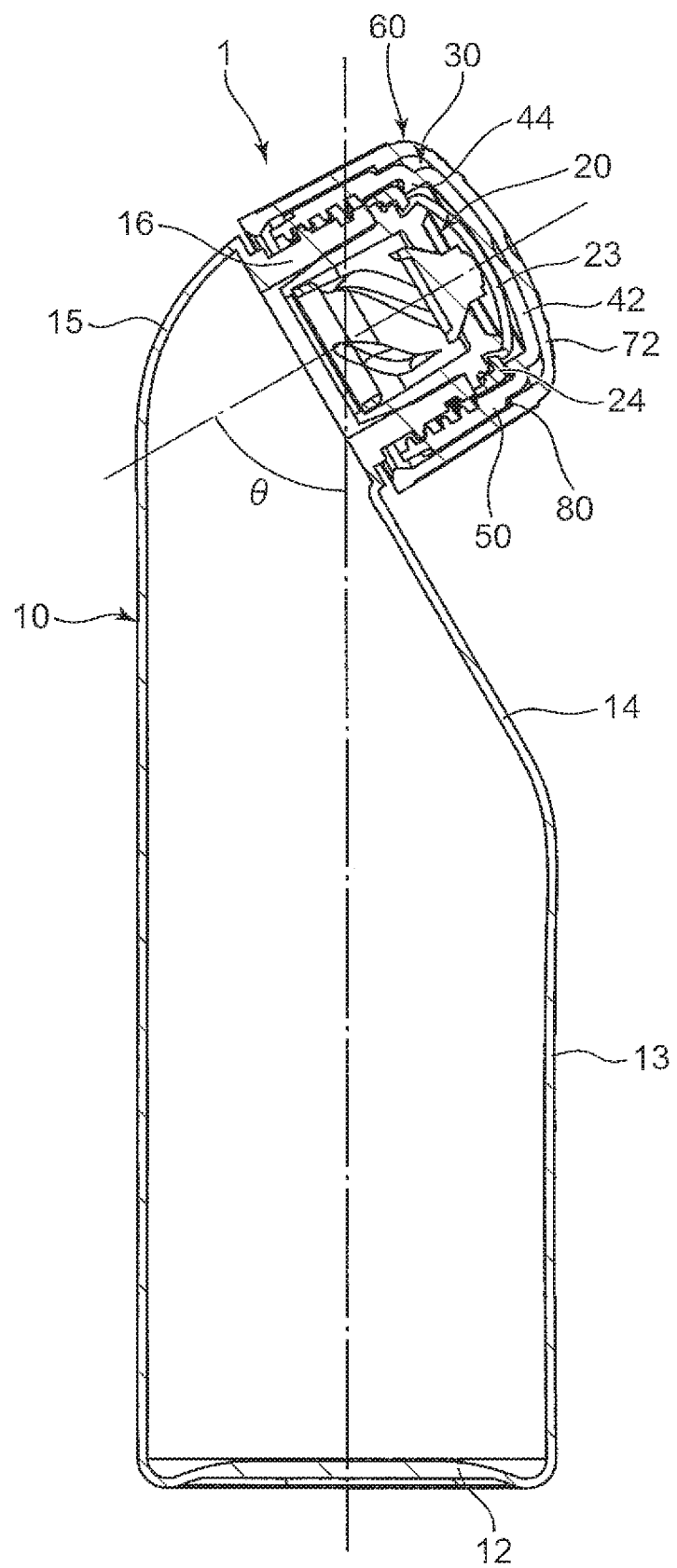
FIG. 4 is a cross-sectional view of the liquid medicine supply device in FIG. 1.
Figure 5:
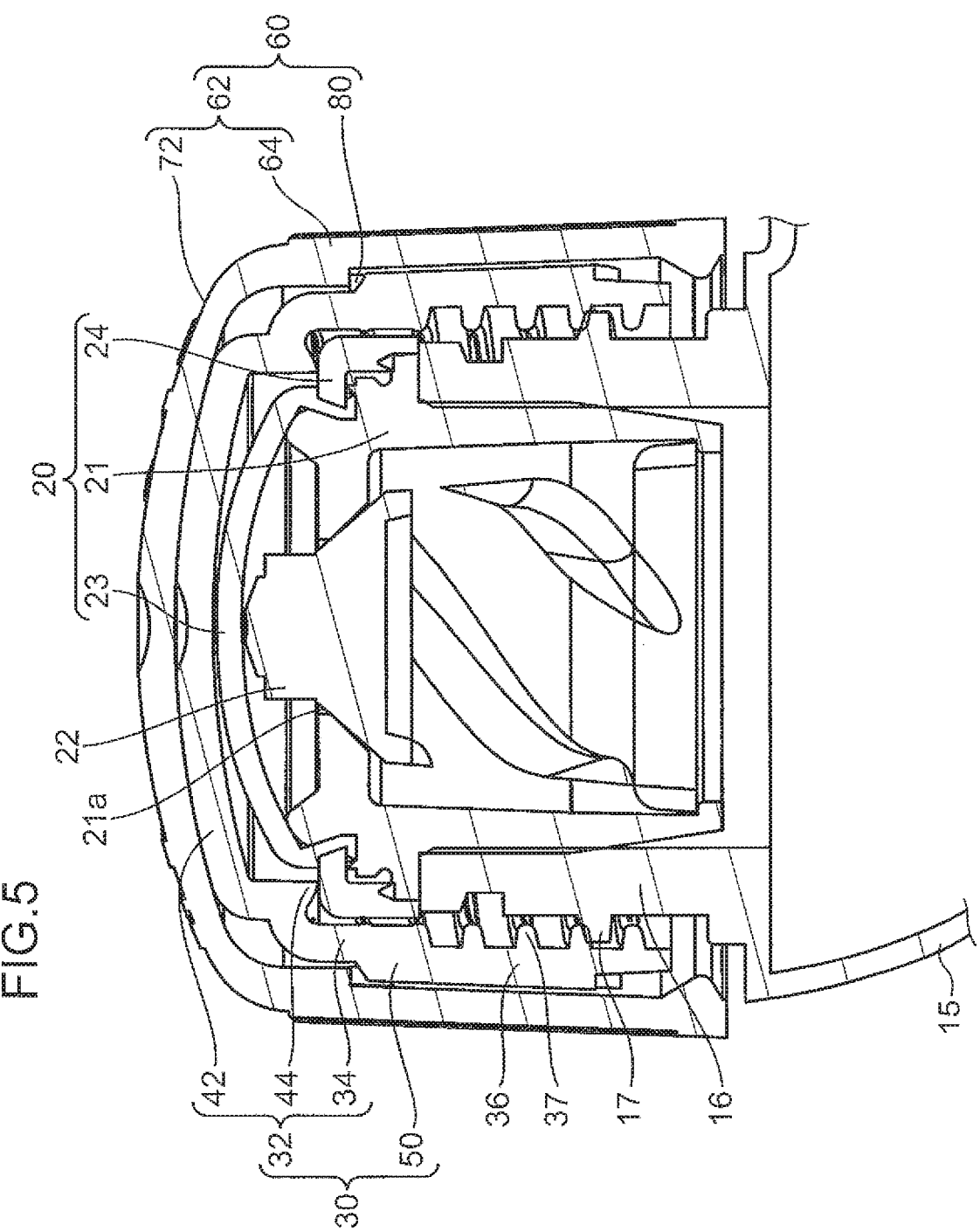
FIG. 5 is an enlarged view of a mouth, an interior cap and an exterior cap in FIG. 4.

As shown in FIGS. 1, 4, and 5, for example, the liquid medicine supply device 1 includes a container 10, a stopper 20, an interior cap 30 and an exterior cap 60. The interior and exterior caps 30, 60 include a ratchet mechanism as the child resistant function. The ratchet mechanism includes a structure configured to allow an integral rotation of the exterior and interior caps 60, 30 when the exterior cap 60 is rotated under a condition of the exterior cap 60 pressed against the interior cap 30, the structure being configured to allow a rotation of the exterior cap 60 relative to the interior cap 30 (not transmitted) when the exterior cap 60 is rotated under a condition of the exterior cap 60 which is not pressed against the interior cap 30. The ratchet mechanism is described below.

The container 10 includes a containing portion 11, a neck 15 and a mouth 16.

The containing portion 11 contains a liquid medicine. In detail, the containing portion 11 includes a bottom wall 12, a body 13 and a contractive portion 14.

Figure 3:
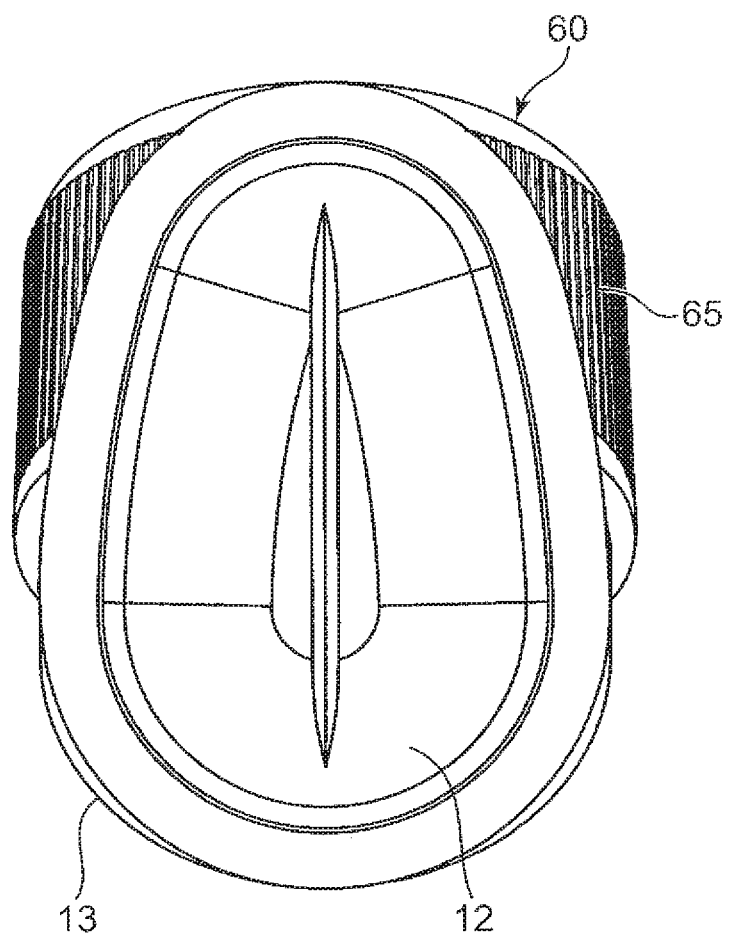
FIG. 3 is a bottom view of the liquid medicine supply device in FIG. 1.

The body 13 extends upward from an edge of the bottom wall 12. The body 13 is tubular. As shown in FIGS. 1 and 3, the body 13 is longer in length in first directions (vertical direction in FIG. 3) perpendicularly intersecting an axial direction of the body 13 than in second directions (lateral direction in FIG. 3) perpendicularly intersecting both the axial direction and the first directions of the body 13.

The contractive portion 14 is connected to the upper end of the body 13. The contractive portion 14 becomes gradually smaller in diameter in a direction from the body 13 to the upper end of the contractive portion 14.

The neck 15 is connected to the upper end of the contractive portion 14.

Figure 2:
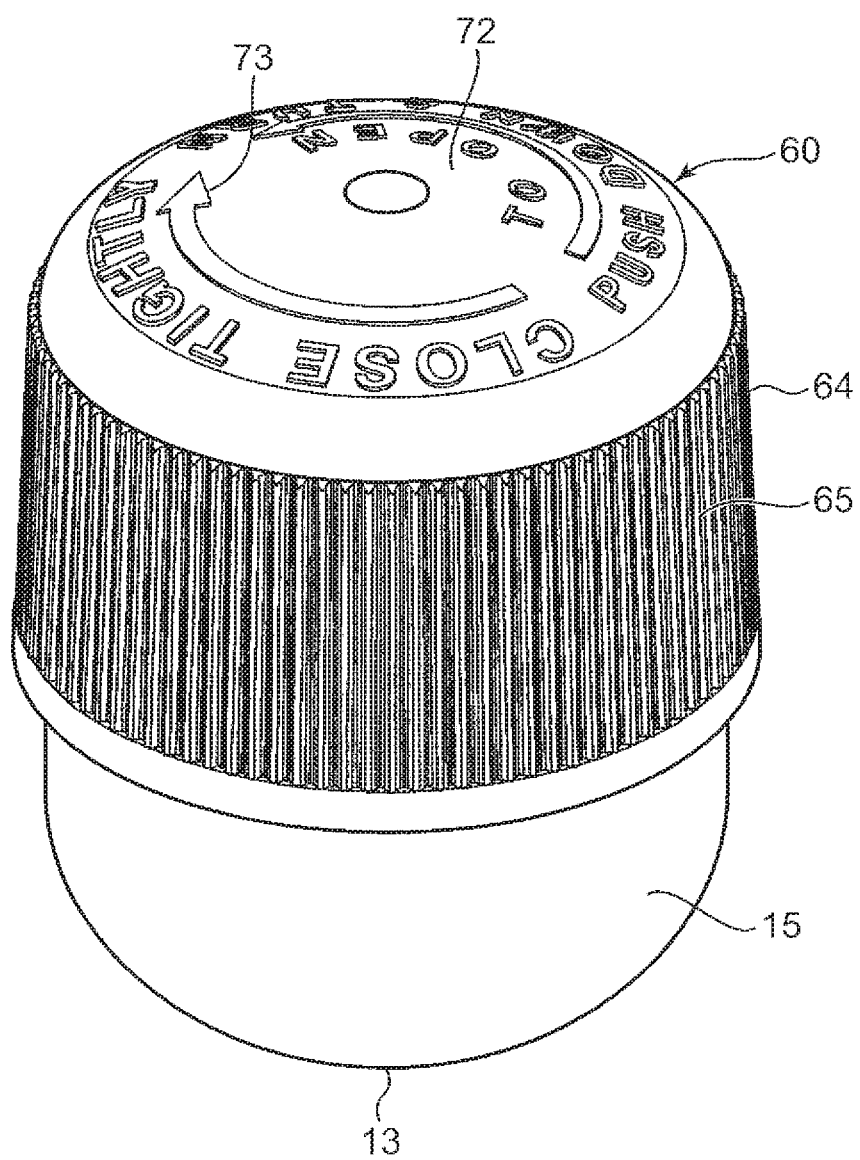
FIG. 2 is a plan view of the liquid medicine supply device in FIG. 1.

The mouth 16 is connected to the upper end of the neck 15. The mouth 16 is cylindrical. The mouth 16 includes a male thread 17. As shown in FIGS. 1 and 4, the central axis of the mouth 16 is inclined from the central axis of the containing portion 11 at a predetermined angle θ. With regard to the present embodiment, the predetermined angle θ is 60°. In order to prevent infants and children from accidentally opening the liquid medicine supply device 1, the predetermined angle θ is preferably 15° to 75°. As shown in FIG. 2, the axial direction of the mouth 16 is defined so that a line formed when the axial direction of the mouth 16 is projected on a projection plane from a plan view of the container 10 is in parallel to the first direction.

The stopper 20 is attached to the mouth 16. The stopper 20 includes a stopper main body 21 pressed into the mouth 16, a sponge 23, which is made of polyurethane and covers the stopper main body 21, and a sandwiching portion 24. The sponge 23 is sandwiched between the sandwiching portion 24 and the stopper main body 21. The stopper main body 21 includes an urging portion 22 configured to urge the sponge 23 against the interior cap 30 (right upward in FIG. 4). The urging portion 22 has a shape operable to close a liquid medicine outlet 21a of the stopper main body 21. An edge of the sponge 23 is sandwiched between the sandwiching portion 24 and the stopper main body 21. When the liquid medicine supply device 1 is used (under a removal condition of the interior and exterior caps 30, 60), the sponge 23 is made in contact with the supplied part, so that the sponge 23 and the urging portion 22 are pressed by an urging force of the urging portion 22. Consequently, the liquid medicine flows through the liquid medicine outlet 21a. The sponge 23 absorbs the liquid medicine flown through the liquid medicine outlet 21a and supplies the liquid medicine to the supplied part.

Next, the interior cap 30 is described with reference to FIGS. 5 to 8. The interior cap 30 is removably connected to the mouth 16. The interior cap 30 is connected to the mouth 16 to tightly close the container 10. The interior cap 30 is made of synthetic resin. The interior cap 30 includes an interior-cap main body 32, and engaging portions 50 which are on an outer surface of the interior-cap main body 32 to constitute a part of the ratchet mechanism.

The interior-cap main body 32 includes a female thread 37 with which the male thread 17 is engaged. The interior-cap main body 32 has a shape operable to close an opening of the mouth 16. In detail, the interior-cap main body 32 includes an interior-cap circular wall 34 with the female thread 37, an interior-cap upper wall 42 and a contact ring 44.

The interior-cap circular wall 34 includes a cylindrical large-outer-diameter portion 36, and a small-outer-diameter portion 38 which is smaller in outer diameter than the large-outer-diameter portion 36. The female thread 37 is on the inner curved surface of the large-outer-diameter portion 36.

Figure 6:
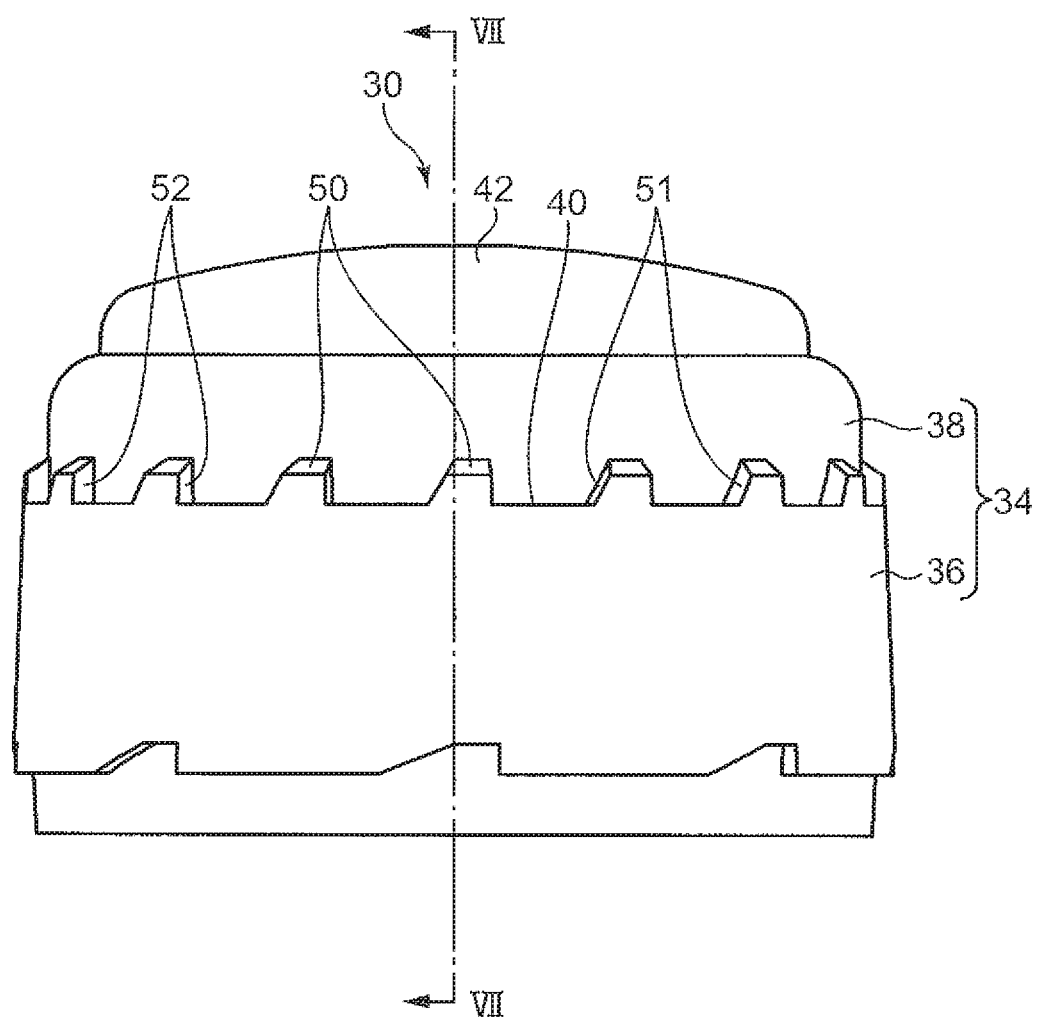
FIG. 6 is a front view of the interior cap.
Figure 7:
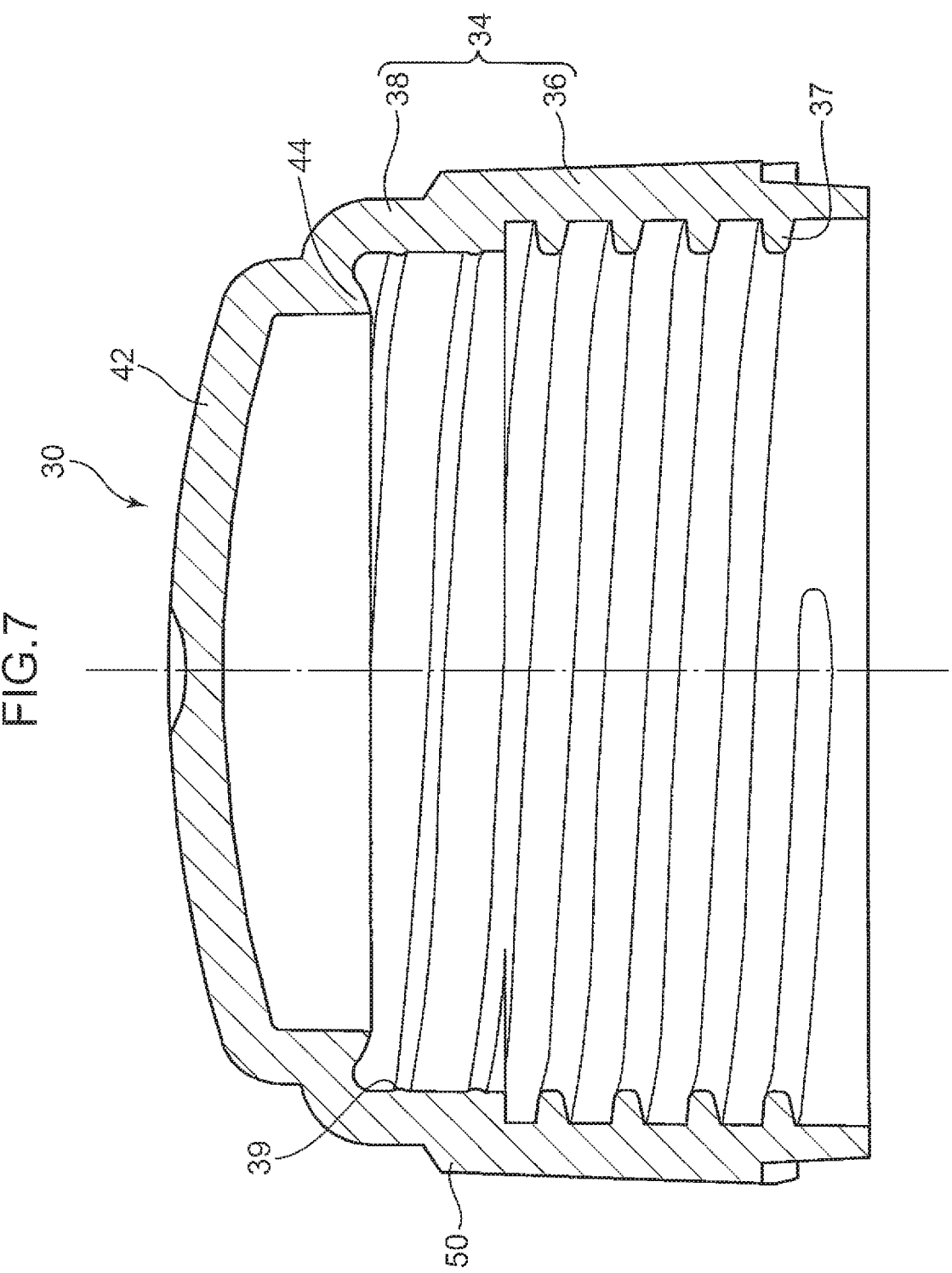
FIG. 7 is a cross-sectional view taken along line VII-VII in FIG. 6.
Figure 8:
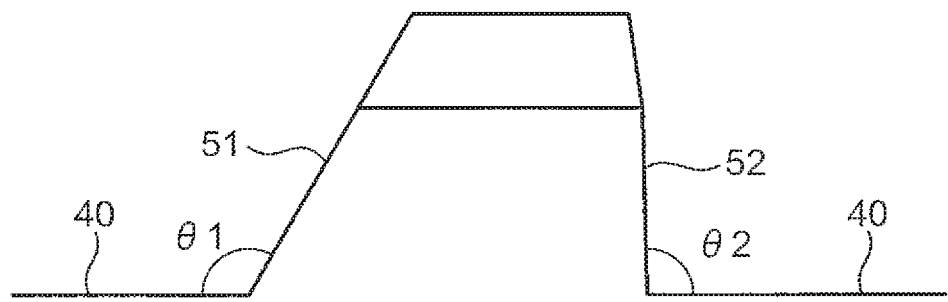
FIG. 8 is an enlarged view of an engaging portion in FIG. 6.

The small-outer-diameter portion 38 is connected to the upper end of the large-outer-diameter portion 36. As shown in FIGS. 6 and 8, the outer surface of the interior-cap circular wall 34 includes an inner arrangement surface 40 at the boundary between the large-outer-diameter portion 36 and the small-outer-diameter portion 38. The inner arrangement surface 40 has a shape perpendicularly intersecting the axial direction of the interior-cap circular wall 34. As shown in FIG. 7, the inner surface of the small-outer-diameter portion 38 may include a small female thread 39. The small female thread 39 is not engaged with the male thread 17 of the mouth 16. With regard to the present embodiment, a projection amount of the female thread 37 from an inner surface of the large-outer-diameter portion 36 is 0.95 mm. On the other hand, a projection amount of the small female thread 39 from the inner surface of the small-outer-diameter portion 38 is approximately 0.1 mm.

The interior-cap upper wall 42 is connected to the upper end of the interior-cap circular wall 34, The interior-cap upper wall 42 has a disk shape. The interior-cap upper wall 42 protrudes outward (upward in FIG. 6) in the axial direction of the interior-cap circular wall 34.

The contact ring 44 protrudes inward (rightward in FIGS. 5 and 7) from the bottom surface (inner surface) of the interior-cap upper wall 42. The contact ring 44 is annular around the central axis of the interior-cap upper wall 42. As shown in FIG. 5, when the female thread 37 is engaged with the male thread 17, the contact ring 44 comes into contact with the top surface of the sandwiching portion 24 of the stopper 20 to tightly close the container 10.

The engaging portions 50 are on the inner arrangement surface 40. The engaging portions 50 protrude toward the exterior cap 60 (upward in FIG. 6) from the inner arrangement surface 40. The engaging portions 50 are arranged at regular intervals in the circumferential direction of the interior-cap circular wall 34.

As shown in FIGS. 5 and 7, the engaging portions 50 are distant from the contact ring 44 in the radial direction of the interior-cap circular wall 34. The engaging portions 50 are distant from the female thread 37 in the axial direction of the interior-cap circular wall 34. In short, the engaging portions 50 are between the contact ring 44 and the female thread 37 in the axial direction of the interior-cap circular wall 34. The engaging portions 50 are on the inner arrangement surface 40 which is outside the contact ring 44 in the radial direction of the interior-cap circular wall 34.

As shown in FIG. 8, each of the engaging portions 50 includes an open-time-pressed-surface 51 and a close-time-pressed-surface 52. These are described below.

Next, the exterior cap 60 is described with reference to FIGS. 5, 9 to 11. The exterior cap 60 is attached to the outside of the interior cap 30. The exterior cap 60 is movable relative to the interior cap 30 in the axial direction of the interior cap 30. The exterior cap 60 is made of synthetic resin. The exterior cap 60 includes an exterior-cap main body 62, and engaged portions 80 which are on the inner surface of the exterior-cap main body 62. The engaged portions 80 and the engaging portions 50 constitute the ratchet mechanism.

The exterior-cap main body 62 has a shape operable to cover the interior-cap main body 32. The exterior-cap main body 62 includes an exterior-cap circular wall 64 and an exterior-cap upper wall 72.

Figure 9:
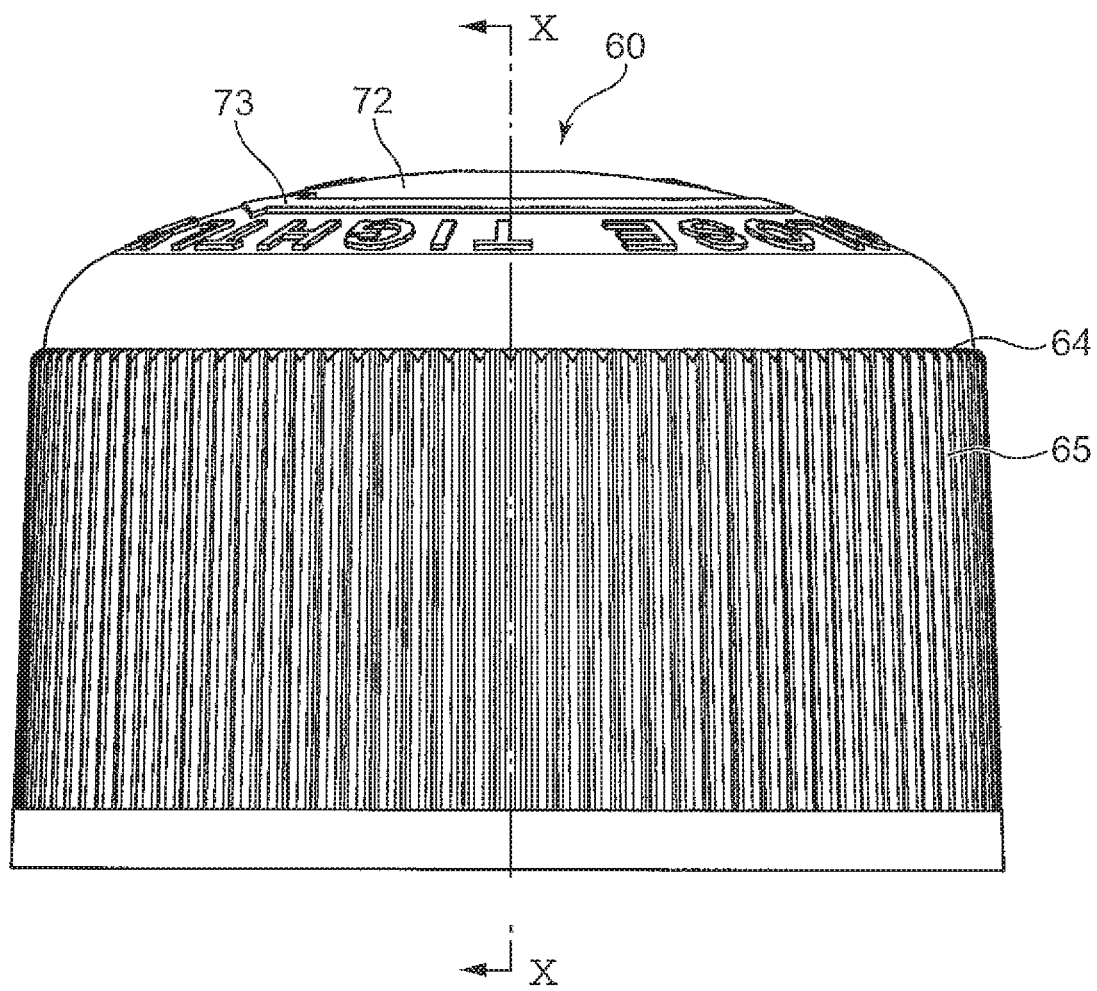
FIG. 9 is a front view of the exterior cap.

The exterior-cap circular wall 64 includes a cylindrical large-inner-diameter portion 66, and a small-inner-diameter portion 68 which is smaller in inner diameter than the large-inner-diameter portion 66. As shown in FIG. 9, for example, an outer curved surface of the exterior-cap circular wall 64 includes a knurled pattern 65. As shown in FIG. 1, the exterior-cap circular wall 64 is larger in outer diameter than the neck 15.

Figure 10:
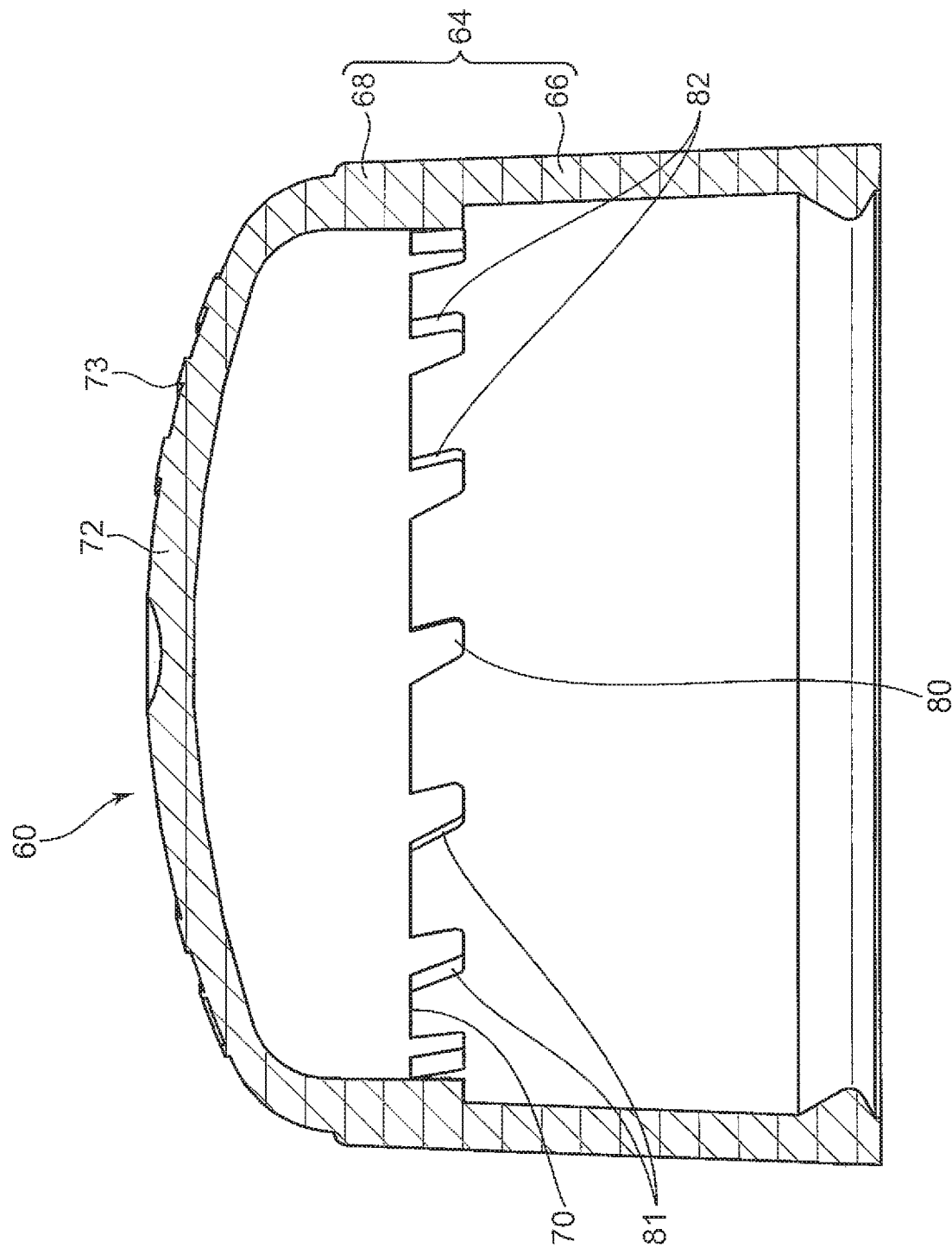
FIG. 10 is a cross-sectional view taken along line X-X in FIG. 9.

The small-inner-diameter portion 68 is connected to the upper end of the large-inner-diameter portion 66. As shown in FIG. 10, the inner surface of the exterior-cap circular wall 64 includes an outer arrangement surface 70 at the boundary between the large-inner-diameter portion 66 and the small-inner-diameter portion 68. The outer arrangement surface 70 has a shape perpendicularly intersecting the axial direction of the exterior-cap circular wall 64.

The exterior-cap upper wall 72 is connected to the upper end of the exterior-cap circular wall 64, The exterior-cap upper wall 72 has a disk shape. The exterior-cap upper wall 72 protrudes outward (upward in FIG. 9) in the axial direction of the exterior-cap circular wall 64. A label 73 is on the top surface of the exterior-cap upper wall 72. The label 73 protrudes upward from the top surface of the exterior-cap upper wall 72.

Each of the engaged portions 80 has a shape operable to be engaged with each of the engaging portions 50. The engaged portions 80 are on the outer arrangement surface 70. The engaged portions 80 protrude toward the interior cap 30 (rightward in FIG. 10) from the outer arrangement surface 70. The engaged portions 80 are arranged at regular intervals in the circumferential direction of the exterior-cap circular wall 64. The engaged portions 80 are as many as the engaging portions 50.

Each of the engaged portions 80 includes an open-time-pressing-surface 81 and a close-time-pressing-surface 82. Each of the open-time-pressing-surfaces 81 and each of the close-time-pressing-surfaces 82, and the open-time-pressed-surface 51 and the close-time-pressed-surface 52 of the interior cap 30 are described.

The open-time-pressed-surface 51 is pressed by the open-time-pressing-surface 81 of the engaged portion 80 when the exterior-cap main body 62 is rotated in a direction (counterclockwise) to open the exterior-cap main body 62 under a pressed state in which the exterior-cap main body 62 is pressed against the interior-cap main body 32. The close-time-pressed-surface 52 is pressed by the close-time-pressing-surface 82 of the engaged portion 80 when the pressed exterior-cap main body 62 is rotated in a direction (clockwise) to close the exterior-cap main body 62 under the pressed state. Each of the pressing surfaces 81, 82 do not press each of the pressed surfaces 51, 52 even when the exterior-cap main body 62 is rotated under a condition of the exterior-cap main body which is not pressed against the interior-cap main body 32.

As shown in FIG. 8, a first angle $\theta 1$ is defined between the open-time-pressed-surface 51 and the inner arrangement surface 40. Normally, the first angle $\theta 1$ is 90° to 150°. Preferably, the first angle $\theta 1$ is 110° to 150° and in the range of 1.57 to 10 times as large as the predetermined angle $\theta$. More preferably, the first angle $\theta 1$ is in the range of 1.57 to 3.75 times as large as the predetermined angle $\theta$. Further preferably, the first angle $\theta 1$ is in the range of 1.57 to 3.5 times as large as the predetermined angle $\theta$. With regard to the present embodiment, the first angle $\theta 1$ is the predetermined angle $\theta$ multiplied by two. In short, the first angle $\theta 1$ is 120°. A second angle $\theta 2$ is defined between the close-time-pressed-surface 52 and the inner arrangement surface 40. Preferably, the second angle $\theta 2$ is 60° to 110° and in the range of 0.86 to 7.33 times as large as the predetermined angle $\theta$. More preferably, the second angle $\theta 2$ is in the range of 0.86 to 2.75 times as large as the predetermined angle $\theta$. Further preferably, the second angle $\theta 2$ is in the range of 1 to 2.25 times as large as the predetermined angle $\theta$. With regard to the present embodiment, the second angle $\theta 2$ is the predetermined angle $\theta$ multiplied by 1.5. In short, the second angle $\theta 2$ is 90°.

Figure 11:
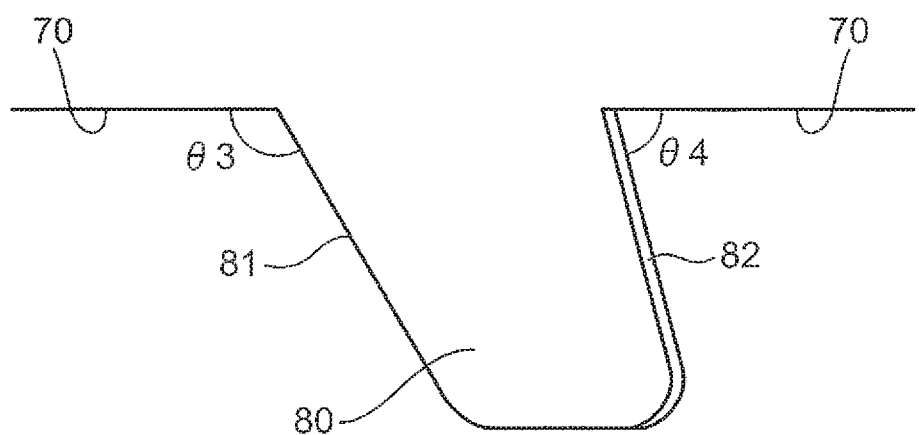
FIG. 11 is an enlarged view of an engaged portion in FIG. 10.

As shown in FIG. 11, a third angle $\theta 3$ is defined between the open-time-pressing-surface 81 and the outer arrangement surface 70. Normally, the third angle $\theta 3$ is 90° to 150°. Preferably, the third angle $\theta 3$ is 110° to 150° and in the range of 1.57 to 10 times as large as the predetermined angle $\theta$. More preferably, the third angle $\theta 3$ is in the range of 1.57 to 3.75 times as large as the predetermined angle $\theta$. Further preferably, the third angle θ3 is in the range of 1.57 to 3.5 times as large as the predetermined angle θ. With regard to the present embodiment, the third angle θ3 is the predetermined angle θ multiplied by two. In short, the third angle θ3 is 120°. A fourth angle θ4 is defined between the close-time-pressing-surface 82 and the outer arrangement surface 70. Preferably and normally, the fourth angle θ4 is 60° to 110° and in the range of 0.86 to 7.33 times as large as the predetermined angle θ. More preferably, the fourth angle θ4 is in the range of 0.86 to 2.75 times as large as the predetermined angle θ. Further preferably, the fourth angle θ4 is in the range of 0.93 to 2.25 times as large as the predetermined angle θ. With regard to the present embodiment, the fourth angle θ4 is the predetermined angle θ multiplied by 1.3. In short, the fourth angle θ4 is 75°.

Next, it is described how to remove the exterior and interior caps 60, 30.

Figure 12:
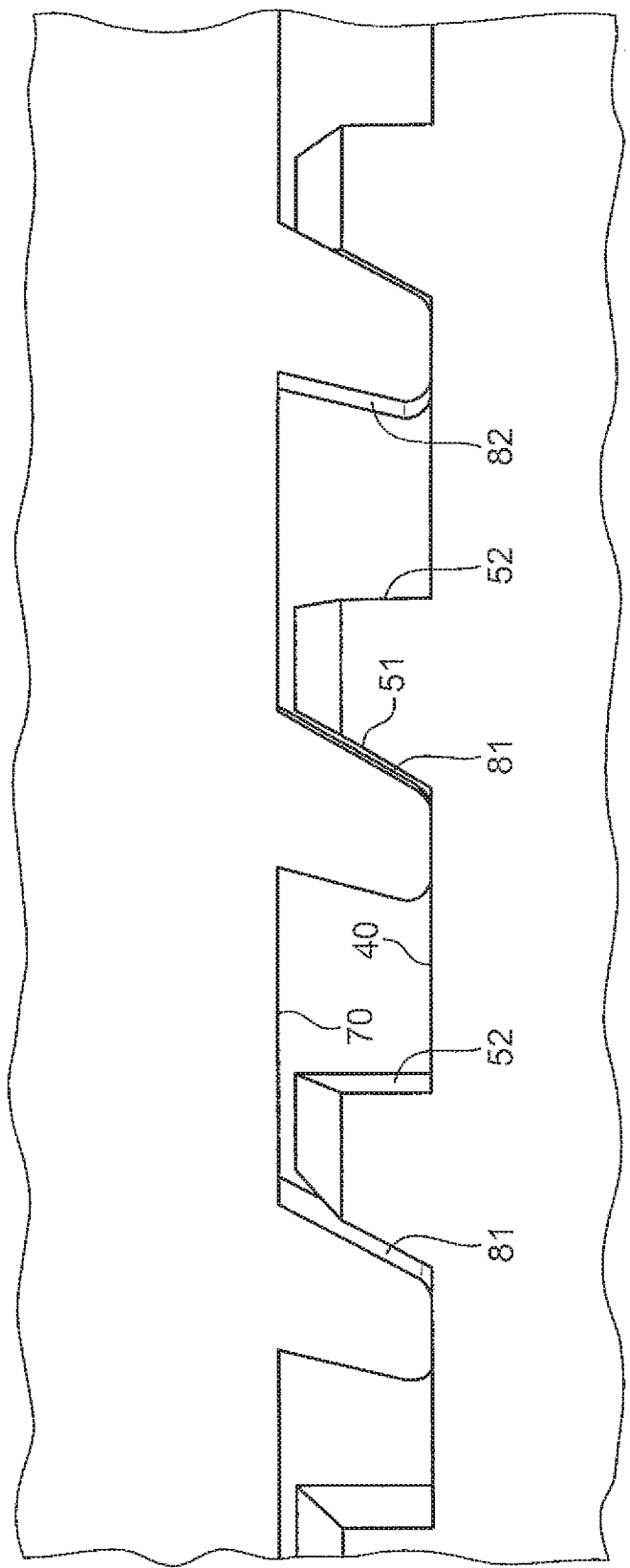
FIG. 12 is a view showing an open-time-pressing-surface of engaged portions pressing an open-time-pressed-surface of engaging portions.

First, the body 13 or the contractive portion 14 is held with one hand whereas the exterior cap 60 is held with the other hand. Then, the exterior cap 60 is pressed against the interior cap 30 (mouth 16). Consequently, the ratchet mechanism engages. In detail, the lower ends of the engaged portions 80 comes into contact with the inner arrangement surface 40, as shown in FIG. 12. With regard to the present embodiment, since the axial direction of the mouth 16 is inclined from the axial direction of the containing portion 11 at the predetermined angle θ, pressing the exterior cap 60 to engage the ratchet mechanism is difficult for infants and children without understanding how to remove the exterior and interior caps 60, 30.

Then, the exterior cap 60 is rotated counterclockwise relative to the mouth 16 under the pressed state in which the exterior cap 60 is pressed against the interior cap 30 (the engaged state of the ratchet mechanism). Consequently, the exterior and interior caps 60, 30 are rotated counterclockwise relative to the mouth 16 since the open-time-pressing-surfaces 81 of the engaged portions 80 press the respective open-time-pressed-surfaces 51 of the engaging portions 50. Consequently, the caps 30, 60 are removed from the container 10.

On the other hand, even if the exterior cap 60 is rotated counterclockwise without being pressed against the interior cap 30 (without engagement of the ratchet mechanism), the open-time-pressing-surfaces 81 do not press the open-time-pressed-surfaces 51, or a sufficient force is not transmitted from the open-time-pressing-surfaces 81 to the open-time-pressed-surfaces 51. Therefore, the exterior cap 60 is rotated relative to the interior cap 30 (the interior cap 30 does not rotate). Consequently, the caps 60, 30 are not removed from the container 10.

As described above, with regard to the present embodiment, the central axis of the mouth 16 is inclined from the axial direction of the containing portion 11 at the predetermined angle θ. Therefore, in order to press the exterior cap 60 against the interior cap 30 or the mouth 16 with one hand, an external force resisting the pressing force has to be applied to the containing portion 11. Therefore, in order to remove the interior and exterior caps 30, 60 from the mouth 16, the containing portion 11 has to be held with one hand while the exterior cap 60 pressed against the interior cap 30 or the mouth 16 with the other hand (the ratchet mechanism engages) has to be rotated with the other hand in a direction in which the exterior cap 60 is removed from the mouth 16. Therefore, infants and children are prevented from accidentally opening the liquid medicine supply device 1.

Since the mouth 16 is opened so that the mouth 16 is oriented toward one of the longitudinal directions (the first directions) of the body on a cross section perpendicularly intersecting the axial direction of the body 13, it is easy to apply a force pressing the exterior cap 60 against the interior cap 30 with one hand while the body 13 is held with the other hand. Therefore, intentional removal of the exterior and interior caps 60, 30 is easy for adults understanding how to remove the exterior and interior caps 60, 30 from the container 10.

Since the exterior cap 60 is larger in outer diameter than the neck 15, the neck 15 does not interfere with fingers holding the exterior cap 60. Therefore, the exterior cap 60 is easily opened or closed.

The first and third angles θ1, θ3 are 90° to 150° and in the range of 1.57 to 10 times as large as the predetermined angle θ. Therefore, it becomes easy to intentionally remove the exterior and interior caps 60, 30. In detail, since the axial direction of the mouth 16 is inclined from the axial direction of the containing portion 11 at the predetermined angle θ, it is difficult to apply a force pressing the exterior-cap main body 62 against the interior-cap main body 32. However, a force transmitted from the open-time-pressing-surfaces 81 to the open-time-pressed-surfaces 51 is obtained when the exterior-cap main body 62 is rotated under the pressed state since the first and third angles θ1, θ3 are 90° to 150° and in the range of 1.57 to 10 times as large as the predetermined angle θ.

The mouth 16 is reliably closed with the exterior and interior caps 60, 30 since the second and fourth angles θ2 are 60° to 110° and in the range of 0.86 to 7.33 times as large as the predetermined angle θ. The mouth 16 is easily closed even under a worn condition of the close-time-pressing-surfaces 82.

The contact ring 44 is distant from the engaging portions 50 in the radial direction of the interior-cap circular wall 34. In short, the contact ring 44 does not overlap the engaging portions 50 in the axial direction of the interior-cap circular wall 34. Therefore, the engaging portions 50 do not cause sink marks on the contact ring 44 when synthetic resin is shaped into the interior cap 30 in a mold. Therefore, the container 10 is tightly sealed.

The engaging portions 50 are distant from the female thread 37 in the axial direction of the interior-cap circular wall 34. In short, the engaging portions 50 do not overlap the female thread 37 in the radial direction of the interior-cap circular wall 34. Therefore, the engaging portions 50 do not cause sink marks on the female thread 37 when synthetic resin is shaped into the interior cap 30 in a mold.

The inner arrangement surface 40 is a part of the outer surface of the interior-cap circular wall 34, the part of the outer surface of the interior-cap circular wall 34 being outside the contact ring 44 in the radial direction of the interior-cap circular wall 34. This configuration therefore increases torque transmitted from the exterior-cap main body 62 to the interior-cap main body 32 as compared to a configuration in which the engaging portions 50 are on an outer surface of a part of the interior-cap main body 32, the part of the interior-cap main body 32 being inside the contact ring 44 in the radial direction of the interior-cap circular wall 34, so that the exterior and interior caps 60, 30 are easily opened or closed.

The aforementioned embodiment disclosed herein is exemplified in all respects and should not be regarded as restrictive. The scope of the present invention is not determined from the aforementioned description of the present embodiment, but from the claims. Further, the scope of the present invention includes all variations within the spirit and scope of the claim and the equivalents.

For example, an urging means may be provided to urge the exterior cap 60 so that the exterior cap 60 is distant from the interior cap 30 without an external force acting on the exterior cap 60. Consequently, infants and children are reliably prevented from accidentally opening the liquid medicine supply device (reliable prevention from unintentional engagement of the ratchet mechanism).

REFERENCE SIGNS 1 liquid medicine supply device
10 container
11 containing portion
13 body
15 neck
16 mouth
17 male thread
20 stopper
30 interior cap
32 interior-cap main body
34 interior-cap circular wall
36 large-outer-diameter portion
37 female thread
38 small-outer-diameter portion
40 inner arrangement surface
42 interior-cap upper wall
44 contact ring
50 engaging portion (ratchet mechanism)
51 open-time-pressed-surface
52 close-time-pressed-surface
60 exterior cap
62 exterior-cap main body
64 exterior-cap circular wall
66 large-inner-diameter portion
68 small-inner-diameter portion
70 outer arrangement surface
72 exterior-cap upper wall
80 engaged portion (ratchet mechanism)
81 open-time-pressing-surface
82 close-time-pressing-surface

The invention claimed is:

1. A liquid medicine supply device comprising:
a container including a tubular containing portion for containing liquid medicine, and a cylindrical mouth connected to the containing portion, the cylindrical mouth including a male thread;
an interior cap having a shape operable to close an opening of the mouth, the interior cap including a cylindrical large-outer-diameter portion having an inner circumferential surface on which a female thread is formed to be engaged with the male thread of the mouth, and a small-outer-diameter portion smaller in outer diameter than the large-outer-diameter portion, the small-outer-diameter portion being connected to an upper end of the large-outer-diameter portion to form an inner arrangement surface at a boundary between the large-outer-diameter portion and the small-outer-diameter portion;
an exterior cap attached to an outside of the interior cap and having a shape operable to cover the interior cap; and
a ratchet mechanism configured to allow the exterior and interior caps to be integrally rotated when the exterior cap is rotated relative to the mouth under a pressed state of the exterior cap pressed against the interior cap whereas the ratchet mechanism allows the exterior cap to be rotated relative to the interior cap when the exterior cap is rotated relative to the mouth under a condition of the exterior cap which is not pressed against the interior cap,
wherein an axial direction of the mouth is inclined from an axial direction of the containing portion by a predetermined angle,
wherein the ratchet mechanism includes engaging portions integrally formed with the inner arrangement surface and an outer circumferential surface of the small-outer-diameter portion to surround the outer circumferential surface of the small-outer-diameter portion at intervals so that the engaging portions are distant from the female thread of the large-outer-diameter portion in an axial direction of the interior cap, and engaged portions formed on an inner circumferential surface of the exterior cap to be engaged with the engaging portions under the pressed state,
wherein the small-outer-diameter portion includes an inner circumferential surface from which another female thread protrudes to strengthen the small-outer-diameter portion, the another female thread being not engaged with the male thread of the mouth.

2. The liquid medicine supply device according to claim 1,
wherein the containing portion includes a body which is longer in length in first directions perpendicularly intersecting the axial direction of the containing portion than in second directions perpendicularly intersecting both the axial direction of the containing portion and the first directions, and
wherein the opening of the mouth faces any one of the first directions.

3. The liquid medicine supply device according to claim 1,
wherein the container includes a neck between the containing portion and the mouth, and
wherein the exterior cap is larger in outer diameter than the neck.

4. The liquid medicine supply device according to claim 1,
wherein the engaging portions protrude toward the exterior cap from the inner arrangement surface in an axial direction of the interior cap,
wherein the exterior cap includes an outer arrangement surface on which the engaged portions are arranged,
wherein the engaged portions protrude toward the interior cap from the outer arrangement surface in an axial direction of the exterior cap,
wherein each of the engaging portions includes:
an open-time-pressed-surface configured to be pressed by one of the engaged portions when the exterior cap is rotated in a direction to open the exterior cap under the pressed state,
a close-time-pressed-surface configured to be pressed by one of the engaged portions when the exterior cap is rotated in a direction to close the exterior cap under the pressed state,
wherein each of the engaged portions includes:
an open-time-pressing-surface configured to press the open-time-pressed-surface when the exterior cap is rotated in the direction to open the exterior cap under the pressed state, and
a close-time-pressing-surface configured to press the close-time-pressed-surface when the exterior cap is rotated in the direction to close the exterior cap under the pressed state.

5. The liquid medicine supply device according to claim 4,
wherein the inner arrangement surface has a shape perpendicularly intersecting the axial direction of the interior cap,
wherein an angle defined between the open-time-pressed-surface and the inner arrangement surface is in a range of 1.57 to 10 times as large as the predetermined angle,
wherein the outer arrangement surface has a shape perpendicularly intersecting the axial direction of the exterior cap, and
wherein an angle defined between the open-time-pressing-surface and the outer arrangement surface is in a range of 1.57 to 10 times as large as the predetermined angle.

6. The liquid medicine supply device according to claim 5,
wherein an angle defined between the close-time-pressed-surface and the inner arrangement surface is in a range of 0.86 to 7.33 times as large as the predetermined angle, and
wherein an angle defined between the close-time-pressing-surface and the outer arrangement surface is in a range of 0.86 to 7.33 times as large as the predetermined angle.

7. The liquid medicine supply device according to claim 4,
wherein the interior cap includes:
an interior-cap upper wall connected to an upper end of the small-outer-diameter portion; and
a contact ring protruding toward the mouth from an inner surface of the interior-cap upper wall to come into contact with the mouth or a stopper attached to the mouth so that the contact ring tightly closes the container, the contact ring having an annular shape around a central axis of the interior cap, and
wherein the contact ring is distant from the engaging portions in a radial direction of the interior cap.

8. The liquid medicine supply device according to claim 7,
wherein the inner arrangement surface is formed at a portion outside the contact ring in the radial direction of the interior cap.

9. The liquid medicine supply device according to claim 2,
wherein the container includes a neck between the containing portion and the mouth, and
wherein the exterior cap is larger in outer diameter than the neck.

10. The liquid medicine supply device according to claim 2,
wherein the engaging portions protrude toward the exterior cap from the inner arrangement surface in an axial direction of the interior cap,
wherein the exterior cap includes an outer arrangement surface on which the engaged portions are arranged,
wherein the engaged portions protrude toward the interior cap from the outer arrangement surface in an axial direction of the exterior cap,
wherein each of the engaging portions includes:
an open-time-pressed-surface configured to be pressed by one of the engaged portions when the exterior cap is rotated in a direction to open the exterior cap under the pressed state,
a close-time-pressed-surface configured to be pressed by one of the engaged portions when the exterior cap is rotated in a direction to close the exterior cap under the pressed state,
wherein each of the engaged portions includes:
an open-time-pressing-surface configured to press the open-time-pressed-surface when the exterior cap is rotated in the direction to open the exterior cap under the pressed state, and
a close-time-pressing-surface configured to press the close-time-pressed-surface when the exterior cap is rotated in the direction to close the exterior cap under the pressed state.

11. The liquid medicine supply device according to claim 3,
wherein the engaging portions protrude toward the exterior cap from the inner arrangement surface in an axial direction of the interior cap,
wherein the exterior cap includes an outer arrangement surface on which the engaged portions are arranged,
wherein the engaged portions protrude toward the interior cap from the outer arrangement surface in an axial direction of the exterior cap,
wherein each of the engaging portions includes:
an open-time-pressed-surface configured to be pressed by one of the engaged portions when the exterior cap is rotated in a direction to open the exterior cap under the pressed state,
a close-time-pressed-surface configured to be pressed by one of the engaged portions when the exterior cap is rotated in a direction to close the exterior cap under the pressed state,
wherein each of the engaged portions includes:
an open-time-pressing-surface configured to press the open-time-pressed-surface when the exterior cap is rotated in the direction to open the exterior cap under the pressed state, and
a close-time-pressing-surface configured to press the close-time-pressed-surface when the exterior cap is rotated in the direction to close the exterior cap under the pressed state.

12. The liquid medicine supply device according to claim 5,
wherein the interior cap includes:
an interior-cap upper wall connected to an upper end of the small-outer-diameter portion; and
a contact ring protruding toward the mouth from an inner surface of the interior-cap upper wall to come into contact with the mouth or a stopper attached to the mouth so that the contact ring tightly closes the container, the contact ring having an annular shape around a central axis of the interior cap, and
wherein the contact ring is distant from the engaging portions in a radial direction of the interior cap.

13. The liquid medicine supply device according to claim 6,
wherein the interior cap includes:
an interior-cap upper wall connected to an upper end of the small-outer-diameter portion; and
a contact ring protruding toward the mouth from an inner surface of the interior-cap upper wall to come into contact with the mouth or a stopper attached to the mouth so that the contact ring tightly closes the container, the contact ring having an annular shape around a central axis of the interior cap, and wherein the contact ring is distant from the engaging portions in a radial direction of the interior cap.

\* \* \* \* \*